United States Patent [19]

Bundy et al.

[11] 4,024,167

[45] May 17, 1977

[54] 11-DIOXY-CIS-4,5-DIDEHYDRO-PGF COMPOUNDS

[75] Inventors: Gordon L. Bundy, Kalamazoo; Norman A. Nelson, Galesburg, both of Mich.

[73] Assignee: The Upjohn Company, Kalamazoo, Mich.

[22] Filed: Jan. 12, 1976

[21] Appl. No.: 648,266

Related U.S. Application Data

[62] Division of Ser. No. 548,586, Feb. 10, 1975, Pat. No. 3,987,072.

[52] U.S. Cl. .............................. 260/410; 260/410.5; 260/410.9 R; 260/413; 260/468 D; 260/514 D
[51] Int. Cl.² ....................................... C07C 177/00
[58] Field of Search ........ 260/410.9 R, 413, 468 D, 260/514 D

[56] References Cited

UNITED STATES PATENTS

| | | | |
|---|---|---|---|
| 3,917,668 | 11/1975 | Abraham et al. | 260/468 |
| 3,932,479 | 1/1976 | Bernady et al. | 260/448 |

*Primary Examiner*—Robert Mirstl
*Attorney, Agent, or Firm*—Robert A. Armitage

[57] ABSTRACT

This invention relates to a group of cis-4,5-didehydro-11-deoxy-$PG_1$ analogs having variable chain length, optional methyl substitution in the methyl-terminated side-chain, and processes for making them. These compounds are useful for a variety of pharmacological purposes, including ulcer treatment, inhibition of platelet aggregation, increase of nasal patency, and labor induction at term.

4 Claims, No Drawings

11-DIOXY-CIS-4,5-DIDEHYDRO-PGF COMPOUNDS

This application is a division of Ser. No. 548,586, filed Feb. 10, 1975, now issued as U.S. Pat. No. 3,987,072.

The present invention relates to prostaglandin analogs, for which the essential material constituting a disclosure thereof is incorporated by reference here from U.S. Pat. No. 3,987,072, issued Oct. 19, 1976.

We claim:

1. A compound of the formula

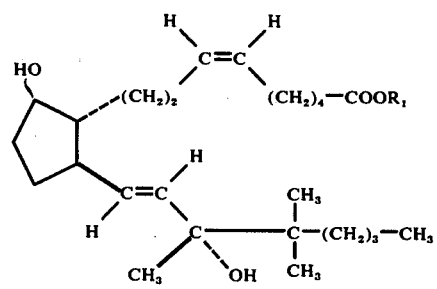

or a mixture comprising that compound and the enantiomer thereof;

wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, 2, or 3 chloro or alkyl of one to 4 carbon atoms, inclusive, or a pharmacologically acceptable cation.

2. A compound of the formula

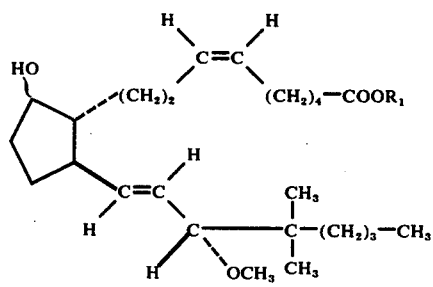

or a mixture comprising that compound and the enantiomer thereof;

wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, 2, or 3 chloro or alkyl of one to 4 carbon atoms, inclusive, or a pharmacologically acceptable cation.

3. A compound of the formula

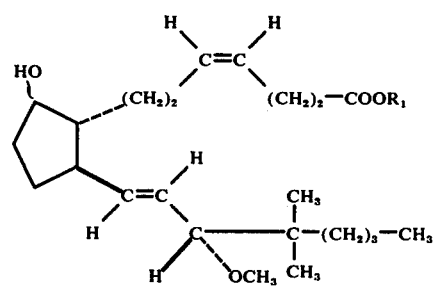

or a mixture comprising that compound and the enantiomer thereof;

wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, 2, or 3 chloro or alkyl of one to 4 carbon atoms, inclusive, or a pharmacologically acceptable cation.

4. cis-4,5-Didehydro-11-deoxy-16,16-dimethyl-$PGF_1$, 15-methyl ether, methyl ester, a compound according to claim 3.

* * * * *